United States Patent [19]

Prakash et al.

[11] Patent Number: 5,109,024

[45] Date of Patent: Apr. 28, 1992

[54] POLYAMINE DERIVATIVES AS ANTINEOPLASTIC AGENTS

[75] Inventors: Nellikunja J. Prakash, Cincinnati; David M. Stemerick, Fairfield; Michael L. Edwards, Cincinnati; Terry L. Bowlin, Maineville, all of Ohio

[73] Assignee: Merrell Dow Pharmaceuticals Inc., Cincinnati, Ohio

[21] Appl. No.: 652,953

[22] Filed: Feb. 8, 1991

Related U.S. Application Data

[63] Continuation-in-part of Ser. No. 602,530, Oct. 24, 1990, abandoned, which is a continuation-in-part of Ser. No. 295,617, Jan. 10, 1989, abandoned, and Ser. No. 449,559, Mar. 26, 1990, Pat. No. 5,020,048, which is a continuation of Ser. No. 295,721, Jan. 10, 1989, abandoned, which is a continuation-in-part of Ser. No. 229,086, Aug. 5, 1988, abandoned, which is a continuation-in-part of Ser. No. 10,380, Feb. 3, 1987, abandoned, said Ser. No. 295,617, Jan. 10, 1989, which is a continuation-in-part of Ser. No. 106,197, Oct. 8, 1987, abandoned.

[51] Int. Cl.$^5$ .................... A61K 31/13; C07C 211/09
[52] U.S. Cl. .................... 514/674; 564/512
[58] Field of Search ............... 564/512, 511; 514/674, 514/673

[56] References Cited

FOREIGN PATENT DOCUMENTS

| 0277635 | 8/1988 | European Pat. Off. |
|---|---|---|
| 0311068 | 4/1989 | European Pat. Off. |
| 0378146 | 7/1990 | European Pat. Off. |
| 48601 | 1/1986 | Japan .................... 514/674 |

OTHER PUBLICATIONS

Edwards, Michael L. et al., *J. Med. Chem.* 33:1369–1375 (1990).

*Primary Examiner*—C. Warren Ivy
*Assistant Examiner*—Raymond Covington
*Attorney, Agent, or Firm*—Louis J. Wille

[57] ABSTRACT

The present invention relates to certain novel polyamine compounds of the formula:

$$HN(R)-Z-NH-(CH_2)_7-NH-Z-NH(R)$$

wherein Z is a saturated ($C_2$–$C_6$) alkylene moiety, each R group independently is hydrogen, methyl, ethyl, or n-propyl with the provisos that both R groups cannot be hydrogen and that R is hydrogen or methyl when Z is a branched chain alkylene; or a pharmaceutically acceptable acid addition salt thereof.

26 Claims, No Drawings

POLYAMINE DERIVATIVES AS ANTINEOPLASTIC AGENTS

This application is a continuation-in-part of application Ser. No. 07/602,530, filed Oct. 24, 1990,now abandoned which is a continuation-in-part of application Ser. No. 07/295,617, filed Jan. 10, 1989, now abandoned, and a continuation-in-part of application Ser. No. 07/449,559, filed Mar. 26, 1990 now 455,020,048; wherein application Ser. No. 07/295,617, filed Jan. 10, 1989, now abandoned, is a continuation-in-part of application Ser. No. 07/106,197, filed Oct. 8, 1987, now abandoned; and wherein application Ser. No 07/449,559 now 455,020,048 is a continuation of application Ser. No. 07/295,721, filed Jan. 10, 1989, now abandoned, which is a continuation-in-part of application Ser. No. 07/229,086, filed Aug. 5, 1988, now abandoned, which is a continuation-in-part of application Ser. No. 07/010,380, filed Feb. 3, 1987, now abandoned.

BACKGROUND OF THE INVENTION

Neoplastic disease states in humans are recognized throughout the world as being serious and sometimes life-threatening conditions. These neoplastic diseases, which are characterized by rapidly-proliferating cell growth, have been and continue to be the subject of worldwide research efforts directed toward the identification of therapeutic agents which are effective in the treatment of patients suffering therefrom. Effective therapeutic agents can be characterized as those which prolong the survivability of the patient, which inhibit the rapidly-proliferating cell growth associated with the neoplasm, or which effect a regression of the neoplasm. Research in this area is primarily focused toward identifying agents which would be therapeutically effective in humans. Typically, compounds are tested for antineoplastic activity in small mammals, such as mice, in experiments designed to be predictive of antineoplastic activity not only in those animals but also in humans against specific neoplastic disease states.

It is well known that naturally occurring polyamines, such as spermine and spermidine, play a role in cell growth and proliferation. These naturally occurring polyamines are found in animal cells and are produced in a biosynthetic pathway involving putrescine as a precursor. Putrescine is formed by a decarboxylation of ornithine by ornithine decarboxylase (ODC).

It has now been found that certain polyamine derivatives are effective therapeutic agents when administered to an animal suffering from certain neoplastic disease states.

SUMMARY OF THE INVENTION AND DETAILED DESCRIPTION

This invention relates to methods of use of certain polyamine derivatives in the treatment of patients suffering from certain neoplastic disease states and to pharmaceutical compositions containing these polyamine derivatives. The invention also relates to certain novel polyamine derivatives.

More specifically, this invention relates to a method for the treatment of patients suffering from certain neoplastic disease states which comprises administering a therapeutically effective amount of a compound of the formula (I):

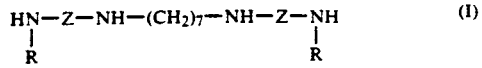

wherein Z is a saturated ($C_2$–$C_6$) alkylene moiety, each R group independently is hydrogen, methyl, ethyl, or n-propyl with the provisos that both R groups cannot be hydrogen, and that R must be methyl or hydrogen when Z ia a branched chain alkylene; or a pharmaceutically acceptable acid addition salt thereof. Said treatment can optionally comprise conjunctive thereapy with a polyamine oxidase inhibitor.

Furthermore, the present invention relates to the novel compounds of the formula (I), or more specifically to the novel compounds of formula (Ia) and Ib). The novel compounds of formula (Ia) are of the formula:

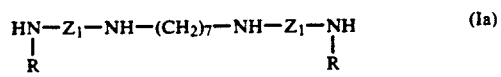

wherein $Z_1$ is a branched chain ($C_2$–$C_6$) alkylene moiety, and each R group independently is hydrogen or methyl with the proviso that both R groups cannot be hydrogen; or a pharmaceutically acceptable acid-addition salt thereof. The novel compounds of formula (Ib) are of the formula:

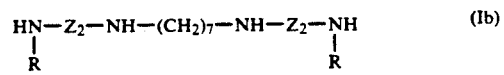

wherein $Z_2$ is a straight chain ($C_2$–$C_6$) alkylene moiety, each R group independently is hydrogen, methyl, ethyl, or n-propyl with he proviso that both R groups cannot be hydrogen; or a pharmaceutically acceptable acid addition salt thereof.

As indicated above, the center alkylene moiety (i.e., "$(CH_2)_7$") of compounds of the formula (I) is a saturated, straight-chain hydrocarbylene radical comprising 7 carbon atoms. As used herein, the term "Z" is understood to mean a saturated hydrocarbylene radical of straight or branched-chain configuration comprising 2 to 6 carbon atoms including, but not limited to, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH(CH_3)CH_2$—, —$CH(CH_3)CH_2CH_2$—, —$CH_2CH(CH_3)CH_2$—and the like.

Compounds of the formula (I) can be used according to the present invention as pharmaceutically acceptable acid addition salts thereof. The term "pharmaceutically acceptable acid addition salt" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. The hydrochloric acid addition salts are preferred. The selection and preparation of pharmaceutically acceptable non-toxic acid addition salts are within the ability of one of ordinary skill in the art utilizing procedures and techniques well known and appreciated in the art.

In general, the compounds of formula (I) may be prepared by chemical reactions analogously known in the art. The choice of any specific route of preparation is dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (I).

A preferred route for the synthesis of compounds of the formula (I) wherein Z is —$CH_2CH_2CH_2$—, but also applicable by analogy for other compounds of formula (I) wherein Z is an alkyl-substituted propylene group (such as —$CH(CH_3)CH_2CH_2$—), is presented in Reaction Scheme A.

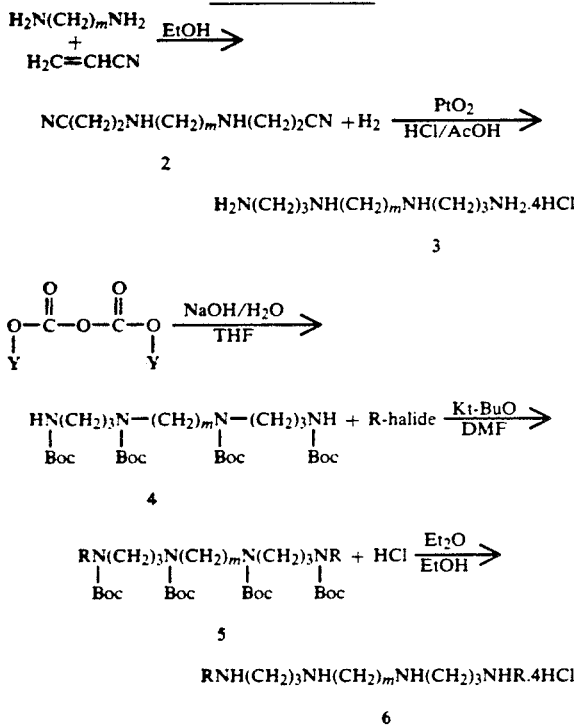

wherein m is 7, R is as defined in formula (I), Boc is the t-butoxycarbonyl protecting group, and Y is tert-butyl.

The initial step of this process entails an N-alkylation of the appropriate diamine with 2 equivalents of acrylonitrile by heating reactants, either in a suitable solvent or neat, according to standard conditions well known in the art. The resulting cyano derivatives (2) are chemically reduced by reaction with hydrogen in the presence of a catalyst ($PtO_2$) in a suitable solvent, such as acetic acid containing 8 equivalents of hydrochloric or hydrobromic acid, to produce the resulting hydrohalic salts according to standard procedures well known in the art. Of course, other reducing systems, e.g., reduction with lithium aluminum hydride, may also be utilized to produce compounds of formula (3). Following the preparation of these compounds the hydrohalic salts are neutralized with base and the nitrogen atoms are protected, preferably with di-t-butyldicarbonate according to standard operating conditions well known in the art. The tetra N-protected amines (4) are alkylated by reacting (4) with the appropriate alkyl halides (chloro or bromo) in the presence of potassium butoxide according to standard alkylation procedures well known in the art. When it is desired to provide compounds of the formula (I) wherein both R groups are the same, about 3 equivalents of the alkyl halide is reacted. When it is desired to provide compounds of the formula (I) wherein the R groups are not the same, monosubstitution of compounds of formula (4) is effected by reacting about 1 to about 1.5 equivalents of the alkyl halide with subsequent isolation of the monosubstituted compound according to standard procedures well known in the art and optionally further reacting the monosubstituted compound with the desired different alkyl halide. Following alkylation the N-protective groups of compound (5) are removed by standard procedures, e.g., treatment with acid, preferably HCl, in the presence of a suitable solvent or solvent system, e.g., diethyloxide in ethanol, to obtain the desired products (6).

alternatively, compounds of formula (3) and their otherwise prepared homologs may be subjected to a reductive alkylationusing an appropriate aldehyde. The reduction is effected by hydrogenation in the presence of $PtO_2$ or sodium cyanoborohydride according to well known procedures. This procedure does not require protection of the nitrogen atoms of the intermediates.

A preferred route for the preparation of compounds of formula (I) wherein Z is —$CH_2(CH_2)_2CH_2$—, but which is also applicable by analogy to those compounds wherein Z is any straight chain, is presented in Reaction Scheme B.

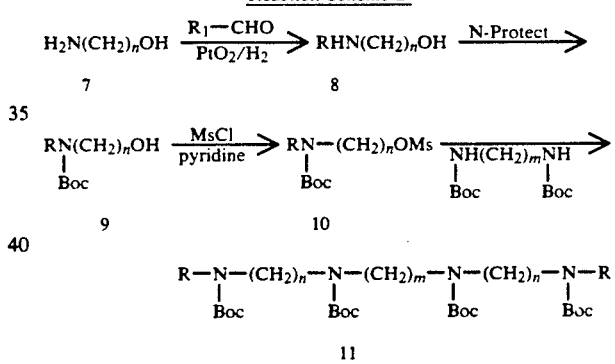

wherein m is 7, n is an integer 2 to 6 describing a straight chain alkylene moiety, Boc is the t-butoxycarbonyl protecting group, R is as defined in formula (I), Ms is mesyl and $R_1$ is hydrogen, methyl or ethyl.

This synthesis is initiated by reductive alkylation techniques well known in the art using an amino alcohol (7) and an appropriate aldehyde to form R- substituted amino alcohols (8). The nitrogen atom is protected, preferably with di-t-butyldicarbonate, according to standard operating conditions well known in the art, to yield the N-protected amino alcohols (9) which are converted to their mesylates (10) by known reaction conditions, e.g., reaction with mesylchloride in the presence of pyridine, preferably in a solvent such as $CH_2Cl_2$.

The mesylate is subjected to alkylation with an N-protected diamine (i.e., BocNH($CH_2)_m$NHBoc) in the presence of potassium t-butoxide in a solvent SuCh as DMF. The so-produced tetra N-protected tetramines (11) are deprotected as in Scheme A. In essence the foregoing reductive alkylation, N-protection, mesylation, alkylation and deprotection procedures all employ techniques and reaction conditions which are well known in the art.

In those instances wherein it is desired to prepare compounds of formula (I) wherein Z is —CH$_2$—CH$_2$—, it is preferred to employ Reaction Scheme C to obtain the necessary intermediates (14) which could be subjected to the alkylation procedures discussed above in Scheme A. wherein m is 7.

The foregoing N-alkylation entails the reaction of an appropriate dihaloalkane (13) with excess quantities (10×) of ethylene diamine (12) by heating the reactants at reflux temperatures in a suitable solvent, e.g., ethanol.

Reaction Scheme C

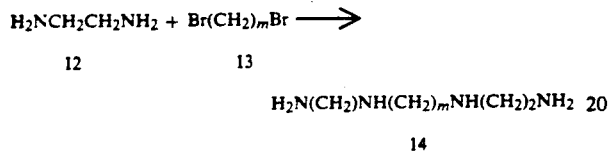

Preparation of the final products bearing the desired R substituents on the terminal nitrogen atoms of the intermediates (14) may be effected by N-protection, alkylation with the appropriate alkyl halide, and deprotection in an analogous manner to that described for Reaction Scheme A. Preferably, the alkylation can be carried out by the reductive alkylation procedures without N-protection as alternatively described for Reaction Scheme A.

Based upon standard laboratory experimental techniques and procedures well known and appreciated by those skilled in the art, as well as upon comparisons with compounds of known usefulness, the compounds of formula (I) can be used in he treatment of patients suffering from those neoplastic disease states which are dependent upon polyamine biosynthesis for their growth. Such neoplastic diseases include: leukemias, including but not limited to acute lymphoblastic, chronic lymphocytic, acute myloblastic and chronic mylocytic; carcinomas, includin but not limited to those of the cervix, sesophagus, stomach, small intestines, colon and lungs; sarcomas, including but not limited to oesteroma, osteosarcoma, lipoma, liposarcoma, hemangioma and hemangiosarcoma; melanomas, including amelanotic and melanotic; and mixed types of neoplasias such as, for example, carcinosarcoma, lymphoid tissue type, folicullar reticulum, cell sarcoma and Hodgkins Disease. Of course, one skilled in the art will recognize that not every compound of formula (I) will be effective against each of the neoplastic disease states, and that selection of the most appropriate compound is within the ability of one of ordinary skill in the art and will depend on a variety of factors including assessment of results obtained in standard animal tumor models.

As used herein, the term "patient" refers to a warm-blooded animal such as a mammal which is afflicted with a neoplastic disease state. It is understood that dogs, cats, rats, mice, horses, bovine cattle, sheep, and humans are examples of animals within the scope of the meaning of the term.

The term "neoplastic disease" as used herein refers to an abnormal state or condition characterized by rapidly proliferating cell growth or neoplasm such as a carcinoma, a sarcoma, a leukemia, and a melanoma.

Treatment of a patient afflicted with a neoplastic disease state comprises administering to such patient an amount of a compound of the formula (I) which is therapeutically effective in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm. It is believed that prolonging the survivability of a patient, beyond being a significant advantageous effect in and of itself, also indicates that the growth of the neoplasm has been controlled.

In effecting treatment of a patient afflicted with a neoplastic disease state a compound of formula (I) can be administered parenterally in any manner which makes (I) bioavailable in effective amounts including for example, by intraperitoneal (i.p.), subcutaneous (s.c.), or intravenous (i.v.) injection. Administration by intravenous injection is preferred.

A therapeutically effective dose or amount can readily be determined by the attending diagnostician and is a function of a number of factors including, but not limited to, the species of mammal, its size, age and general health, the specific neoplasm involved, the degree of involvement, the stage of development of the neoplasm, the compound selected and mode of administration, the bioavailability characteristics of the preparation administered, the dose regimen selected, and use of concomitant medication. The correct amount for any specific situation can be readily determined by those skilled in the art using conventional range finding techniques and analogous results observed under other circumstances. A therapeutically effective amount of (I) will vary from about 1 milligram per kilogram of body weight per day (mg/kg/day) to about 500 mg/kg/day and preferably will be about 5 mg/kg/day to about 50 mg/kg/day. It is believed that compounds of the formula (I) administered at the above doses to a patient suffering from a neoplastic disease are therapeutically effective in controlling the growth of one or more neoplastic disease states or in prolonging the survivability of the patient beyond that expected in the absence of such treatment.

A preferred embodiment of the present invention, relating to a method of treatment of patients suffering from a neoplastic disease state, comprises administering to said patient a therapeutically effective amount of a compound of the formula (I) in conjunctive therapy with an effective amount of a polyamine oxidase (PAO) inhibitor. The term "conjunctive therapy" contemplates coadministration of (I) along with a PAO inhibitor at essentially the same time, or treatment of the patient with a PAO inhibitor prior to or after treatment with (I). The PAO inhibitor is administered in an amount effective in substantially inhibiting PAO in the patient. When a compound of the formula (I) and a PAO inhibitor are administered in conjunctive therapy the PAO inhibitor may produce an additive or synergistic effect with (I). Thus, the dose of (I) required to produce a therapeutic effect in the patient may be less when administered in conjunctive therapy with an effective amount of a PAO inhibitor than that required when (I) is administered alone.

Various PAO inhibitors can be used including, but not limited to, N,N'-bis(2,3-butadienyl)-1,4-butanediamine, N-(2,3-butadienyl)-N'-(methyl)-1,4-butanediamine, or pharmaceutically acceptable acid addition salts thereof as described in U.S. Pat. No. 4,551,550 which is incorporated herein by reference. N,N'-bis(2,3-butadienyl)-1,4-butanediamine is preferred as the PAO inhibitor for conjunctive therapy.

In effecting conjunctive therapy of a patient afflicted with a neoplastic disease state the PAO inhibitor can be administered parenterally in any manner which makes the PAO inhibitor bioavailable in effective amounts including, for example, by intraperitoneal (i.p.), subcutaneous (s.c.) or intravenous (i.v.) injection. Administration by intravenous injection is preferred.

An effective dose of the PAO inhibitor can readily be determined by the attending diagnostician and is a function of a number of factors including, but not limited to, the species of mammal, its size, age and general health, the specific neoplasm involved, the degree of involvement, the stage of development of the neoplasm, the mode of administration, the bioavailability characteristics of the compounds and preparation administered, the dose regimen selected, and use of concomitant medication. The correct amount of any specific situation can be readily determined by those skilled in the art using conventional range finding techniques and analogous results observed under other circumstances. An effective amount of a PAO inhibitor will vary from about 0.1 mg/kg/day to about 100 mg/kg/day and preferably will be about 1 mg/kg/day to about 10 mg/kg/day.

Another embodiment of the present invention relates to pharmaceutical compositions for parenteral administration for compounds of the formula (I). These pharmaceutical compositions comprise a therapeutically effective amount of one or more compounds of the formula (I) in an admixture with one or more pharmaceutically acceptable excipients, with or without, an effective amount of a PAO inhibitor. Such compositions are prepared in conventional manner well known in the art of pharmaceutical science. The amounts of the active ingredient(s) in a unit dosage form and the dosage regimen are adjusted to provide a sustained pharmacologic effect at the dose regimen selected.

Pharmaceutically acceptable excipients are substances that are chemically inert to the active compound(s) and have no detrimental side effects or toxicity to mammals under the conditions of use. Suitable excipients include solvents such as water, alcohol, and propylene glycol, surface active agents, suspending agents, lubricants, flavors, colorants, and the like. Such carriers and excipients are known to those in the art and are disclosed, for example, in texts such as *Remington's Pharmaceutical Manufacturing*, 13th Edition, Mack Publishing Co., Easton, PA (1965).

Injectable dosage forms of a solution or suspension of (I) can be prepared, for example, in a physiologically acceptable diluent with a pharmaceutical carrier which can be a sterile liquid such as water and oils with or without the addition of a surfactant and other pharmaceutically acceptable adjuvants and with or without a PAO inhibitor. Illustrative of oils which can be employed in these preparations are those of petroleum, animal, vegetable or synthetic origin, for example, peanut oil, soybean oil and mineral oil. In general, water, saline, aqueous dextrose and related sugar solution ethanols and glycols such as propylene glycol or polyethylene glycol are preferred liquid carriers, particularly for injectable solutions.

As is well known in the art of pharmaceutical inventions wherein generic classes of compounds are involved, certain subgeneric and certain specific compounds are more efficient in their end-use applications than other members of the generic class. In this invention, those compounds wherein Z is —$CH_2CH_2CH_2$— or —$CH(CH_3)CH_2CH_2$— are most preferred. In all instances it has been shown that the symmetrical compounds are preferred. Compounds for which each R is independently methyl or ethyl are preferred for this method of use and compounds for which both R groups are methyl or both R groups are ethyl are preferred. Compounds for which both R groups are the same moiety are generally preferred.

The following compounds are preferred in the method of use described by the present invention:
N,N'-bis[3-(methylamino)butyl]-1,7-diaminoheptane;
N,N'-bis[3-(ethylamino)propyl]-1,7-diaminoheptane;
N,N'-bis[3-(methylamino)propyl]-1,7-diaminoheptane;
N,N'-bis[3-(methylamino)-2-(methyl)propyl]-1,7-diaminoheptane.

Of these compounds, N,N'-bis[3-(methylamino)butyl]-1,7-diaminoheptane and N,N'-bis[3-(ethylamino)propyl]-1,7-diaminoheptane are most preferred.

Certain novel compounds of the present invention are described by the formula (Ia):

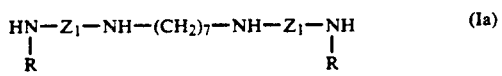

wherein $Z_1$ is a branched chain ($C_2$-$C_6$) alkylene moiety, and each R group independently is hydrogen or methyl with the proviso that both R groups cannot be hydrogen; or a pharmaceutically acceptable acid-addition salt thereof. These compounds are useful as antineoplastic agents as described above for compounds of formula (I). As used herein, the term $Z_1$ is understood to mean a saturated hydrocarbylene radical of branched chain configuration comprising 2 to 6 carbon atoms includin with its scope, but not limited to, *—$CH(CH_3)CH_2CH_2$— and *—$CH(C_2H_5)CH_2CH_2$— wherein * indicates the point of attachment of the terminal amine. Compounds of the formula (Ia) can exist as free amines or as pharmaceutically acceptable acid addition salts thereof as described above for compounds of formula (I).

In general, compounds of the formula (Ia) can be prepared in an analogous manner to that described in Reaction Scheme D.

Reaction Scheme D

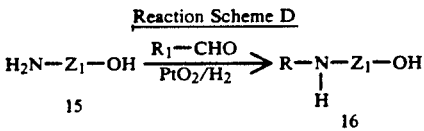

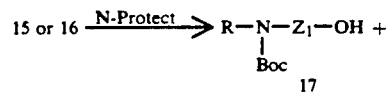

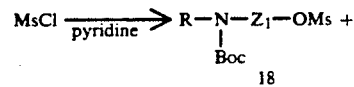

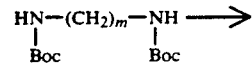

-continued
Reaction Scheme D

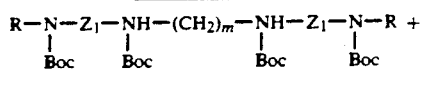

19

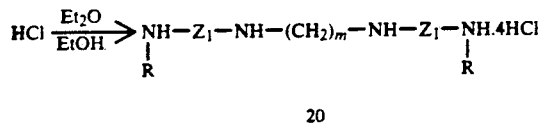

20 wherein m is 7, R and $Z_1$ are as generically defined for formula (Ia), and $R_1$ is hydrogen.

The appropriate primary amino alcohol (15) containing a branched chain hydrocarbylene moiety (i.e., $Z_1$) is prepared by standard procedures well known in the art. If desired, the primary amine can at this point be converted to a secondary amine (16), by a reductive alkylation with the appropriate aldehyde. The amino alcohol is reacted as described in Reaction Scheme A by standard conditions well known in the art to effect protection of the amines with an appropriate N-protecting group such as Boc (17). The mesylates of the N-protected amino alcohols (18) are prepared and are alkylated with the appropriate N-protected diamine (i.e., BocNH(CH$_2$)$_m$NHBoc) using standard procedures well known in the art as discussed for Reaction Scheme B. The so-produced tetra N-protected tetramines (19) are deprotected as in Scheme A to yield compounds of the formula (Ia) In essence, the foregoing reductive alkylation, N-protection, mesylation, alkylation and N-deprotective procedures all employ techniques and reaction conditions which are well known in the art.

Where it is desired to provide a compound of the formula (Ia) wherein each R group is not the same, the substituted mesylates (18) are prepared separately and monoalkylation of the appropriate N-protected diamine (i.e., BocNH(CH$_2$)$_m$NHBoc) is effected by reacting the diamine with about 1.0 to 1.5 equivalents of one of the mesylates (18) with subsequent isolation of the monosubstituted compound and optionally further reacting the monosubstituted compound with the desired different substituted mesylate (18).

In those instances in which it is desired to prepare compounds of the formula (Ia) wherein Z1 is an alkyl-substituted propylene group such as *—CH(Q)CH$_2$CH$_2$—wherein Q is a saturated alkyl radical comprising 1 to 3 carbon atoms of straight or branched chain configuration, Reaction Scheme E can be used to obtain intermediates of the formula (25) which can be subjected to alkylation of the N-terminal groups in a manner analogous to that described in Reaction Scheme A prior to de-protection.

Reaction Scheme E

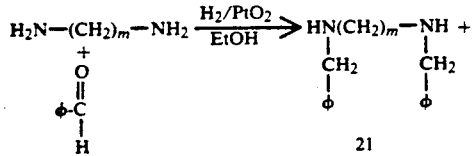

21

-continued
Reaction Scheme E

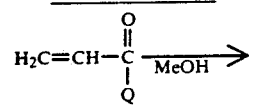

22

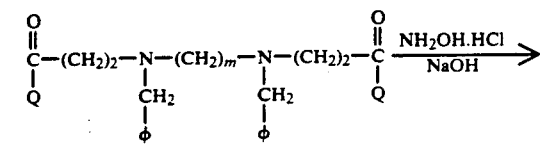

23

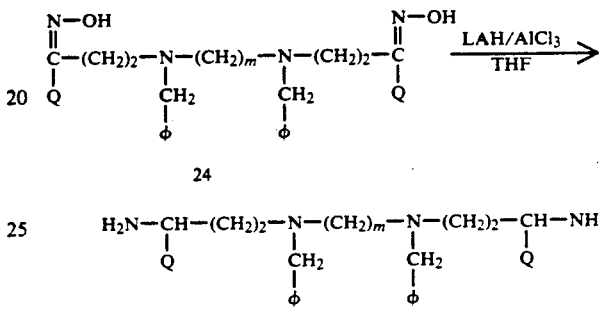

24

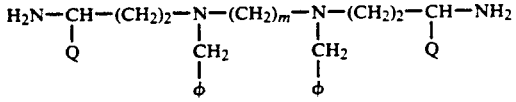

25 wherein m is 7, $\phi$ is phenyl, and Q is as defined above.

The initial step of the process entails a reductive alkylation wherein the appropriate diamine is reacted with hydrogen gas and 2 equivalents of benzaldehyde in the present of a catalyst such as PtO$_2$ to yield the N-protected diamine (21) under standard conditions well known in the art. The N-protected diamine (21) is then alkylated with 2 equivalents of the appropriate vinyl ketone (22) in a suitable solvent such as methanol using standard techniques. The resulting N-substituted diamine (23) is further reacted under standard conditions with hydroxylamine hydrochloride in the presence of base such as NaOH in a suitable solvent such as ethanol/water. The resulting oximes (24) are reduced to the corresponding N-protected di-primary amines (25) by reaction with lithium aluminum hydride (LAH) in the presence of AlCl$_3$. in a suitable solvent such as THF according to standard procedures. The N-protected di-primary amines (25) can be further alkylated with an appropriate aldehyde prior to deprotection in a manner analogous to that described for Reaction Scheme A.

Compounds of formula (Ia) wherein $Z_1$ is *—CH(CH$_3$)CH$_2$CH$_2$— or *—CH(C$_2$H$_5$)CH$_2$CH$_2$—are generally preferred in their end-use application. Compounds of formula (Ia) wherein each R group is the same moiety are also preferred. Compounds of formula (Ia) wherein each R group is methyl or ethyl are particularly preferred.

Of course, it is appreciated that in those instances wherein a compound of formula (Ia) possesses one or more chiral centers, the individual stereoisomers as well as mixtures of stereoisomers are included within the scope of the present invention. For example, the following compounds are specifically included within the scope of formula (I) and (Ia):

(R,R)-N,N'-bis[3-(methylamino)butyl]-1,7-diaminoheptane (S,S)-N,N'-bis[3-(methylamino)butyl]-1,7-diaminoheptane (R,S)-N,N'-bis[3-(methylamino)butyl]-1,7-diaminoheptane.

In order to illustrate the preparation of compounds of formulas (Ia) and (Ib), the following examples are provided. The examples are illustrative only and are not intended to limit the invention in any way. All temperatures are in degrees Celsius and the following abbreviations are used: (g) is grams, (mol) is moles, (ml) is milliliters, (l) is liters, (lb/in$^2$) is pounds per square inch, (TLC) is thin layer chromatography, (THF) is tetrahydrofuran, (DMF) is dimethylformamide (mp) is melting point, (mm/Hg) is pressure expressed as millimeters of mercury, (bp) is boiling point.

EXAMPLE 1

N,N-Bis((3-methylamino)propyl)-1,8-octanediamine tetrahydrochloride

Step A: N,N'-Bis(2-(cyano)ethyl)-1,8-octanediamine

Dissolve 14.4 g (0.1 mol) of 1,8-diaminooctane and 14.5 ml (0.22 mol) of acrylonitrile in 100 ml of ethanol and reflux overnight. Remove the solvent at reduced pressure. Analysis showed the title compound to be >98% pure.

Step B: N,N'-Bis(3-(amino)propyl)1,8-octanediamine tetrahydrochloride

Combine 14.4 g (0.057 mol) of the product of Step A, 200 ml of acetic acid, 30 ml of conc. HCl, and 1.2 g PtO$_2$ and treat the mixture with H$_2$ at 45 lbs/in$^2$ in a shaker flask until H2 is no longer being reacted. Filter the mixture and remove the solvent at reduced pressure. 22.5 g of the title compound is obtained after purification. (R$_f$ is 0.17 for TLC on silica gel developed with 40% conc. ammonia/methanol).

Step C: 1,5,14,18-Tetra(t-butoxycarbonyl)-1,5,14,18-tetraazaoctadecane

Combine 22.5 g (0.052 mol) of the product of Step B with 8.83 g (0.22 mol) of NaOH, 100 ml H$_2$O and 500 ml THF and stir until a homogenous solution is obtained. To this solution add 48.13 g (0.22 mol) of di-t-butyldicarbonate and stir the resulting mixture overnight. Pour the mixture into 1 l. of ethyl acetate, separate the organic layer, and dry over anhydrous MgSO$_4$. Remove the solvent at reduced pressure. Purify the residue by flash chromatography (silica gel), eluting with 25% ethyl acetate/hexane to yield 13.5 g of the title compound (R$_f$ is 0.28 for TLC on silica gel developed with 25% ethyl acetate/hexane).

Step D: 1,18-Bis(methyl)-1,5,14,18-tetra(t-butoxy-carbonyl)-1,5,14,18-tetraazoctadecane Combine 4.3 g (0.0068 mol) of the product of Step C, 0.94 ml (0.015 mol) of iodomethane, 1.69 g (0.015 mol) of potassium t-butoxide, and 15 ml DMF and stir overnight. Remove the solvent at reduced pressure and dissolve the residue in 500 ml ethyl acetate and 200 ml of H$_2$O. Wash the organic layer with 100 ml H$_2$O (2×) and dry over anhydrous MgSO$_4$. Remove the solvent at reduced pressure and purify the residue by flash chromatography (silica gel), eluting with 20% ethyl acetate/hexane to yield 4.4 g of the title compound (R$_f$is 0.20 for TLC on silica gel developed with 20% ethyl acetate/hexane.)

Step E: N,N'-Bis(3-(methylamino)propyl)-1,8-octanediamine tetrahydrochloride

Dissolve 4.4 g (0.0065 mol) of the product of Step D in 3 ml ethanol and treat the solution with 50 ml of 2N HCl in diethyl ether stirring overnight. Filter the resulting mixture and crystallize the residue from methanol/isopropanol/water (20/60/20,v/v/v) at reduced temperature. Filter and dry the product at 79° C. over P$_2$O$_5$ at 0.1 mmHg to yield 2.08 g of the title compound (mp >300° C.). Elemental analysis: calculated, C-44.44, H-9.79, N-12.86, Cl-32.80; Found C-44.44, H-9.82, N-12.95, Cl-32.59, 32.64.

EXAMPLE 2

N,N'-Bis(3-(ethylamino)propyl)-1,8-octanediamine tetrahydrochloride

Step A: 1,18-Bismethyl)-1,5,14,18-tetra(t-butoxy-carbonyl)-1,5,14-18-tetraazaoctadecane Combine 9.5 g (0.0144 mol) of the product of Step C in Example 1, 2.91 g (0.026 mol) of potassium t-butoxide, and 45 ml of DMF and cool to 0° C. Add 2.1 ml (0.026 mol) of iodoethane and stir at 0° C. for 4 hours. Allow the mixture to warm slowly to room temperature and stir overnight. Remove the solvent at reduced pressure and partition the residue between 1400 ml ethyl acetate and 200 ml H$_2$O. Wash the organic layer with 100 ml H$_2$O (2×) and dry over anhydrous MgSO$_4$. Remove the solvent under reduced pressure and purify the residue by flash chromatography (silica gel) eluting with 20% ethyl acetate/hexane to yield 3.3 g of the title compound (R$_f$is 0.26 for TLC on silica gel developed with 20% ethyl acetate/hexane.)

Step B: N,N'-Bis(3-(ethylamino)propyl)-1,8-octanediamine tetrahydrochloride hemihydrate Dissolve 3.3 g (0.0046 mol) of the product of Step A in 7 ml ethanol and treat with 70 ml of 2 N HCl in diethyl ether stirring overnight. Filter the mixture and dry the residue at 70° C. at reduced pressure to yield 1.95 g of the title 46.09, H-10.10, N-11.95, Cl-30.24; Found C-46.23, H-9.94, N-12.11, Cl-29.99.

EXAMPLE 3

N-(3-Aminopropyl)-N'-(3-(ethylamino)propyl)-1,8-octanediamine tetrahydrochloride Step A: 1-Ethyl-1,5,14,18-tetra-(t-butoxycarbonyl)-1,5,14,18-tetraazaoctadecane Follow the procedure described in Step A of Example 2 to yield 2.5 g of the title compound after flash chromatography (R$_f$is 0.17 for TLC On silica gel developed with 20% ethyl aCetate/hexane).

Step B: N-(3-Aminopropyl)-N'-(3-(ethylamino)proyl)-1,8-octanediamine tetrahydrochloride Dissolve 2.5 g (0.0036 mol) of the product of Step A in 5 ml of ethanol and treat with 60 ml of 2 N HCl in diethyl ether stirring overnight. Filter the mixture and dry the residue to yield 1.35 g of the title compound, mp >300° C. Elemental analysis: Calculated, C-43.54, H-9.82, N-12.69, Cl-32.13; Found, C-43.43, H-9.60, 9.55; N-12.60, 12.62; Cl-32.30.

EXAMPLE 4

N,N'-Bis[3-(methylamino)butyl]-1,7-diaminoheptane tetrahydrochloride

Step A N,N'-Bis[(phenyl)methyl]-1,7-heptanediamine

Combine 1,7-diaminoheptane (65.0 g, 0.5 mol), benzaldehyde (106 gm, 1 mol) and platinum oxide (PtO2)[2.0 g]in ethanol (800 ml) and treat the mixture with hydrogen gas (45 lb/in²) until the uptake of gas ceases. Remove the catalyst by filtration and remove the solvent in vacuo. Purify the residue by bulb to bulb distillation to yield 99.4 g of the title compound (bp 191°-195° C. @1.0 mm/Hg).

Step B:
N,N'-Bis[(3-oxo)butyl]-N,N'-bis[(phenyl)methyl]-1,7-diaminoheptane

Dissolve N,N'-bis[(phenyl)methyl]-1,7-heptanediamine (9.3 g, 0.03 mol) in methanol (120 ml) and while stirring the mixture introduce methyl vinyl ketone (5.6 ml, 0.066 mol) in a stream of nitrogen gas. Stir the mixture for 18 hours to yield the title compound.

Step C:
N,N'-Bis[(3-hydroxyimino)butyl]-N,N'-bis[(phenYl)methyl]-1,7-diaminoheptane Cool the reaction mixture obtained in step B to 0° C. and to this mixture add a solution of hydroxylamine hydrochloride (4.38 g, 0.063 mol) and sodium bicarbonate (5.54 g, 0.066 mol) in water (40 ml). Stir the mixture at 0° C. for 30 minutes and then stir at ambient temperature for 2 hours. Remove the solvent in vacuo and partition the residue between water (200 ml) and dichloromethane (200 ml). Wash the aqueous layer 3 times with 200 ml of dichloromethane each time. Combine the organic layers and dry over anhydrous MgSO4. Remove the solvent in vacuo to yield 14.4 g of the title compound. $R_f$ is 0.53 for TLC on silica gel developed with ethyl acetate.

Step D: N,N'-Bis[3-(amino)butyl]-N,N'-bis[(phenyl)methyl]-1,7-diaminoheptane

Add a solution of N,N'-bis[(3-hydroxyimino)butyl]-N,N'-bis[(phenyl)methyl]-1,7-diaminoheptane (14.4 g, 0.03 mol) in THF (70 ml) to a mixture of lithium aluminum hydride (5.8 g, 0.15 mol) in THF (250 ml) and reflux the mixture overnight. Cool the mixture and quench slowly with water (5.8 ml), followed by 15% NaOH (5.8 ml), followed by water (17.4 ml). Filter the mixture and wash the filtrate 3 times with 100 ml of THF each time. Combine the organic layers and remove the solvent in vacuo to obtain 13.4 g of the title compound as a clear viscous oil. $R_f$ is 0.33 for TLC on silica gel developed with 4% conc. ammonia in methanol.

Step E:
2,16-Bis(methyl)-1,5,13,17-tetra(t-butoxycarbonyl)-1,5,13,17-tetraazaheptadecane Combine N,N'-bis[3-(amino)butyl]-N,N'-bis[(phenyl)methyl]-1,7-diaminoheptane (13.4 g, 0.029 mol), Pearlman's Catalyst (2.0 g) and ethanol (90 ml) and treat the mixture with hydrogen gas at 45 lb/in² until gas uptake ceases. Remove the catalyst by filtration and remove the solvent in vacuo to obtain 7.7 g of N,N'-bis[3-(amino)butyl]-1,7-diaminoheptane ($R_f$ is 0.37 for TLC on silica gel developed with 40% conc. ammonia in methanol). Dissolve the residue in dichloromethane (90 ml) and treat the mixture with di-t-butyldicarbonate (26.2 g, 0.12 mol) for 3 hours. Remove the solvent in vacuo and purify the residue by flash chromatography on silica gel eluting with 25% ethyl acetate in hexane to yield 17.1 g of the title compound as a clear oil. $R_f$ is 0.35 for TLC on silica gel developed with 25% ethyl acetate in hexane.

Step F:
1,2,16,17-Tetramethyl-1,5,13,17-tetra(t-butoxycarbonyl)-1,5,13,17-tetraazaheotadecane Combine 2,16-bis(methyl)-1,5,13,17-tetra(t-butoxycarbonyl)-1,5,13,17-tetraazaheptadecane (8.5 g, 0.0126 mol) and sodium hydride (60% in oil)[1.21 g, 0.03 mol]in DMF (75 ml) and stir until hydrogen evolution ceases. To this mixture add methyl iodide (1.88 g, 0.03 mol) and stir for 2 hours. Remove the solvent in vacuo and partition the residue between ethyl acetate (400 ml) and water (200 ml). Dry the organic layer over anhydrous MgSO4 and remove the solvent in vacuo. Purify the residue by flash chromatography on silica gel eluting with 22% ethyl acetate in hexane to yield 3.8 g of the title compound as a clear oil. $R_f$ is 0.22 for TLC on silica gel developed with 20% ethyl acetate in hexane.

Step G:
N,N'-Bis[3-(methylamino)butyl]-1,7-diaminoheptane tetrahydrochloride

Add 1N HCl in methanol (50 ml) to 1,2,16,17-tetramethyl-1,5,13,17-tetra (t-butoxycarbonyl)-1,5,13,17-tetraazaheptadecane (3.8 g, 0.0054 mol) and stir overnight. Remove the solvent in vacuo and recrystallize the residue two times from methanol/acetonitrile (40/60, v/v) to yield 0.74 g of the title compound as a white solid (mp 238°-9 ° C.). $R_f$ is 0.31 for TLC on silica gel developed with 40% conc. ammonia in methanol.

EXAMPLE 5

N,N'-Bis[3-(ethylamino)butyl]-1,7-diaminoheptane tetrahydrochloride

Step A:
1,17-Diethyl-2,16-dimethyl-1,5,13,17-tetra(t-butoxycarbonyl)-1,5,13,17-tetraazaheptadecane Combine 2,16-bis(methyl)-1,5,13,17-tetra(t-butoxycarbonyl)-1,5,13,17-tetraazaheptadecane (8.5 g, 0.0126 mol), made as described in Example 5, and sodium hydride (60% in oil)[1.21 g, 0.03 mol]in DMF (75 ml) and stir until hydrogen evolution ceases. To this mixture add ethyl iodide (4.68 g, 0.03 mol) and stir for 2 hours. Remove the solvent in vacuo and partition the residue between ethyl acetate (400 ml) and water (200 ml). Dry the organic layer over anhydrous MgSO4 and remove the solvent in vacuo. Purify the residue by flash chromatography on silica gel eluting with 22% ethyl acetate in hexane to yield 3.9 g of the title compound as a clear oil. $R_f$ is 0.31 for TLC on silica gel developed with 20% ethyl acetate in hexane.

Step B:
N,N'-Bis[3-(ethylamino)butyl]-1,7-diaminoheptane tetrahydrochloride

Add 1N HCl in methanol (50 ml) to 1,17-diethyl-2,16-dimethyl-1,5,13,17-tetra (t-butoxycarbonyl)-1,5,13,17- tetraazaheptadecane (3.9 g, 0.0054 mol) and stir overnight. Remove the solvent in vacuo and recrystallize the residue two times from methanol/acetonitrile (40/60, v/v) to yield 10 0.90g of the title compound as a white solid (mp 249°-50 ° C.). $R_f$ is 0.56 for TLC on silica gel developed with 40% conc. ammonia in methanol.

EXAMPLE 6
N,N'-Bis[3-(ethylamino)propyl]-1,7-heptanediamine

Steps A and B: 1,5,13,17-Tetraazaheptadecane tetrahydrochloride

Prepare the title compound by the method of Israel et al., J. Med. Chem. 7, 710 (1964).

Step C:
1,5,13,17-Tetra(t-butoxycarbonyl)-1,5,13,17-tetraazaheptadecane

Combine 1,5,13,17-tetraazaheptadecane tetrahydrochloride (3.9 gm, 0.01 mol) and sodium hydroxide (1.76 gm, 0.44 mol) in water (44 ml) and stir until homogeneous. To this mixture add di-t-butyldicarbonate (9.6 gm, 0.044 mol) in THF (88 ml) and stir for 3 hours. Dilute the mixture with ethyl acetate (EtOAc) [300 ml]and separate the organic layer. Dry the organic layer over anhydrous MgSO4 and evaporate in vacuo to obtain a viscous oil. Purify the residue by flash chromatography (silica gel) eluting with 25% EtOAc/hexane to yield 3.0 gm of the title compound. $R_f$ is 0.20 on silica gel plates eluted with 25% EtOAc/hexane.

Step D:
3,7,15,19-Tetra(t-butoxycarbonyl)-3,7,15,19-tetraazaheneicosane

Combine 1,5,13,17-tetra(t-butoxycarbonyl)-1,5,13,17-tetraazaheptadecane (3.0 gm, 0.0046 mol) and sodium hydride (50% in oil) [0.45 gm, 0.011 mol]in DMF (9 ml) and stir the mixture until hydrogen evolution ceases. Add ethyl iodide (0.9 ml, 0.011 mol) and stir the mixture for 18 hours. Evaporate the DMF in vacuo and partition the residue between ethyl acetate (600 ml) and water (200 ml). Separate the organic layer, dry the organic layer over anhydrous MgSO4 and evaporate in vacuo. Purify the residue by flash chromatography (silica gel) eluting with 20% EtOAc/hexane to yield 1.68 gm of the title compound. $R_f$ is 0.5 on silica gel plates eluted with 25% EtOAc/hexane.

Step E:
N,N'-Bis[3-(ethylamino)propyl]-1,7-heptanediamine

Treat 3,7,15,19-tetra(t-butoxycarbonyl)-3,7,15,19-tetraazaheneicosane (1.68 gm, 0.0024 mol) with HCl in methanol (50 ml, 1.0 N) and stir overnight. Filter the mixture and recrystallize the title compound from methanol/water (20:80, v/v) to yield 0.5 gm of the title compound. $R_f$ is 0.39 On silica gel plates eluted with 40% ammonia (concentrated) in methanol; mp 322°-23° C. with degradation.

As a further aspect of the present invention, it has been found that compounds of formulae (I) provide an antineoplastic effect in patients suffering from neoplastic disease states without producing the delayed toxicity effect produced by other similar polyamine neoplastic agents. The following study of the antitumor activity of the compounds of formula (I) against L1210 leukemia illustrates this aspect of the present invention.

Groups of 6 mice (BDF1 male) were inoculated i.p. with 10^5 L1210 leukemia cells on day 0. Test compounds or vehicle (Control group) were administered at the indicated doses starting on day 1 and continuing through day 5 or 9. Relative survival time was determined and expressed as % T/C (mean survival time treated/mean survival time control ×100). Presence or absence of delayed toxicity was determined by an examination o the animal's external appearance and behavior during the study. For example, an emaciated condition is a key indication of delayed toxicity in these studies. The results of these studies are presented in Table 1.

TABLE 1

| Antitumor Activity against L1210 Leukemia[a] | | | |
|---|---|---|---|
| Test Compound | Dose, mg/Kg/day (Days Dosed) | % T/C | Delayed Toxicity |
| 28314 | 10 (days 1-5) | 200 | No |
| 28249 | 10 (days 1-5) | 110 | No |
| 26752 | 10 (days 1-5) | NA[b] | |
| 27393 | 10 (days 1-9) | 112 | Yes |
| 27259 | 10 (days 1-9) | 172 | Yes |
| 26547 | 10 (days 1-9) | 171 | Yes |
| 101060 | 10 (days 1-5) | 180 | No |
| 28600 | 10 (days 1-5) | 132 | No |
| 28516 | 10 (days 1-5) | 200 | Yes |
| 29587 | 10 (days 1-5) | NA[b] | |

[a]Results were obtained through various studies with different Control groups. Mean control survival time varied from 6 to 8 days.
[b]NA = not active at dose studied.

28,314 = $CH_3CH_2-NH-(CH_2)_3-NH-(CH_2)_7-NH-(CH_2)_3-NH-CH_2CH_3$
28249 = $CH_3-NH-(CH_2)_3-NH-(CH_2)_7-NH-(CH_2)_3-NH-CH_3$
26752 = $NH_2-(CH_2)_3-NH-(CH_2)_7-NH-(CH_2)_3-NH_2$
27393 = $CH_3CH_2-NH-(CH_2)_3-NH-(CH_2)_8-NH-(CH_2)_3-NH-CH_2CH_3$
27259 = $CH_3-NH-(CH_2)_3-NH-(CH_2)_8-NH-(CH_2)_3-NH-CH_3$
26547 = $NH_2-(CH_2)_3-NH-(CH_2)_8-NH-(CH_2)_3-NH_2$
101060 = $CH_3-NH-CH(CH_3)CH_2CH_2-NH-(CH_2)_7-NH-CH_2CH_2CH(CH_3)-NH-CH_3$
28600 = $CH_3-NH-CH_2CH(CH_3)CH_2-NH-(CH_2)_7-NH-CH_2CH(CH_3)CH_2-NH-CH_3$
28516 = $NH_2-CH(CH_3)CH_2CH_2-NH-(CH_2)_7-NH-CH_2CH_2CH(CH_3)-NH_2$
29587 = $CH_3CH_2-NH-CH(CH_3)CH_2CH_2-NH-(CH_2)_7-NH-CH_2CH_2CH(CH_3)-NH-CH_2CH_3$

In an additional study, groups of 5 mice (BDF1 male) were inoculated i.p. with 10^5 L1210 leukemia cells on day 0. N,N'-bis[3-(ethylamino)propyl]-1,7-diaminoheptane or vehicle (Control group) were administered at the indicated doses and on the indicated days. The results of this study are presented in Table 2. These results show that at 20 and 40 mg/Kg/day, N,N'-bis[3-(ethylamino)propyl]-1,7-diaminoheptane is effective in providing a curative effect against L1210 leukemia in vivo. In a similar study, N,N'-bis[3-(amino)propyl]-1,8-diaminooctane, administered at a dose of mg/Kg×4 times per day on days 3 through 7, provided a %T/C of 350 but no cures in 6 animals [Edwards et al., J. Med. Chem. 33, 1369 (1990), See Table II infra].

TABLE 2

| Curative Effect of 28314 Against Advanced L1210 Leukemia | | | | |
|---|---|---|---|---|
| Group (n) | Treatment | Dose mg/Kg × doses per day (Days Dosed) | Survival in days (Mean ± S.E.) | % T/C | Cured[a] |
| 1 (5) | Control | — | 7.5 ± 0.4 | — | 0/5 |
| 2 (5) | 28314 | 5 × 4 (days 3, 4) | 16.0 ± 4.0 | — | 0/5 |
| 3 (5) | 28314 | 5 × 4 (days 3, 4, 5) | >45 | — | 5/5 |
| 4 (5) | 28314 | 10 × 4 (days 3, 4) | >45 | — | 5/5 |
| 5 (6) | 26547 | 6.25 × 4 | — | 350[b] | 0/6 |

TABLE 2-continued

| | | Curative Effect of 28314 Against Advanced L1210 Leukemia | | | |
|---|---|---|---|---|---|
| Group (n) | Treatment | Dose mg/Kg × doses per day (Days Dosed) | Survival in days (Mean ± S.E.) | % T/C | Cured[a] |
| | | (days 3 thru 7) | | | |

[a]Mice surviving beyond day 45 were considered cured.
[b]Animals exhibited delayed toxicity.
28,314 = $CH_3CH_2-NH-(CH_2)_3-NH-(CH_2)_7-NH-(CH_2)_3-NH-CH_2CH_3$
26547 = $NH_2-(CH_2)_3-NH-(CH_2)_8-NH-(CH_2)_3-NH_2$ It has also been found that compounds of formula (1) provide an antimetastatic effect in patients suffering from malignant tumors. Metastasis is the process whereby a malignant tumor transfers the neoplastic disease from one tumor site to another so as to form a new foci of disease by dispersal of malignant cells through the circulatory system. The capacity to metastasize is a characteristic of all malignant tumors. Malignant tumors such as colon, breast, lung and prostate carcinomas are particularly prone to metastasis.

C57BL/6 mice were injected intrasplenically on day 0 with MCA-38 colon adenocarcinoma cells ($1 \times 10^5$) so as to induce hepatic metastasis. Liver metastatic foci were determined as described by Bowlin et al. [*Cancer Res.* 50, 5460 (1990)]. Briefly, injected animals were randomly allocated to one of three treatment groups, 6 animals per group, and test compound or vehicle (Control) was administered i.p. at the doses and times indicated in Table 3. Liver metastatic foci were determined on day 14. The results as presented in Table 3 clearly show the antimetastatic effect of Compound in inhibiting liver metastasis.

TABLE 3

| Effect of Compound 28314 on Experimental Murine Liver Metastasis | | |
|---|---|---|
| Test Compound | Liver Metastasis No. foci ± S.E.[a] | Liver Metastasis % Inhibition |
| Control | 220.6 ± 22.2 | — |
| 28314 days 1–5, 5 mg/Kg | 29.2 ± 7.7* | 87 |
| 28314 days 3–8, 5 mg/Kg | 62.3 ± 17.5* | 72 |

[a]S.E. = standard error
28314 = $CH_3CH_2-NH-(CH_2)_3-NH-(CH_2)_7-NH-(CH_2)_3-NH-CH_2CH_3$
*p < 0.001. n = 6

C57BL/6 mice were injected into the footpad on day 0 with 3LL (Lewis lung) carcinoma cells ($1 \times 10^6$) so as to induce lung metastasis. Lung metastatic foci were determined as described by Sunkara et al. [*J. Biological Response Modifiers* 8, 170 (1989)]. Briefly, injected animals were randomly allocated to one of two treatment groups, 6 animals per group, and test compound or vehicle (Control) was administered i.p. at the doses and times indicated in Table 4. Lung metastatic foci were determined on day 18. The results as presented in Table 4 clearly show the antimetastatic effect of Compound 28314 in inhibiting lung metastasis.

TABLE 4

| Effect of Compound 28314 on Experimental Murine Lung Metastasis | | |
|---|---|---|
| Test Compound | Lung Metastasis No. foci ± S.E.[a] (n = 6) | Lung Metastasis % Inhibition |
| Control | 21.3 ± 11.5 | — |
| 28314 days 1–5, 10 mg/Kg | 0 | 100 |

[a]S.E. = standard error
28314 = $CH_3CH_2-NH-(CH_2)_3-NH-(CH_2)_7-NH-(CH_2)_3-NH-CH_2CH_3$

We claim:

1. A compound of the formula:

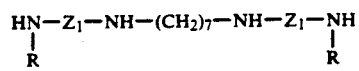

wherein $Z_1$ is a branched chain ($C_2$–$C_6$) alkylene moiety, and each R group independently is hydrogen or methyl with the proviso that both R groups cannot be hydrogen; or a pharmaceutically acceptable acid-addition salt thereof.

2. A compound of claim 1 wherein the compound is N,N'-bis[3-(methylamino)butyl]-1,7-diaminoheptane.

3. A compound of claim 1 wherein the compound is N,N'-bis[3-(methylamino)-2-(methyl)propyl]-1,7-diaminoheptane.

4. A pharmaceutical composition in unit dosage form, which comprises
   (1) one or more pharmaceutically acceptable excipients, and
   (2) a therapeutically effective amount of a compound of the formula:

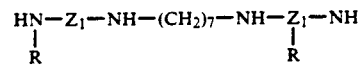

wherein $Z_1$ is a branched chain ($C_2$–$C_6$) alkylene moiety, and each R group independently is hydrogen or methyl with the proviso that both R groups cannot be hydrogen; or a pharmaceutically acceptable acid-addition salt thereof.

5. A pharmaceutical composition according to claim 4 which further comprises an effective amount of a polyamine oxidase inhibitor as an additional ingredient.

6. A compound of the formula:

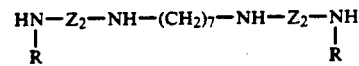

wherein $Z_2$ is a straight chain ($C_2$–$C_6$) alkylene moiety, each R group independently is hydrogen, methyl, ethyl, or n-propyl with the proviso that both R groups cannot be hydrogen; or a pharmaceutically acceptable acid addition salt thereof.

7. A compound of claim 6 wherein the compound is N,N'-bis[3-(ethylamino)propyl]-1,7-diaminoheptane.

8. A compound of claim 6 wherein the compound is N,N'-bis[3-(methylamino)propyl]-1,7-diaminoheptane.

9. A pharmaceutical composition in unit dosage form, which comprises
   (1) one or more pharmaceutically acceptable excipients, and
   (2) a therapeutically effective amount of a compound of the formula:

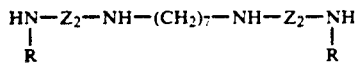

wherein $Z_2$ is a straight chain ($C_2$–$C_6$) alkylene moiety, each R group independently is hydrogen, methyl, ethyl, or n-propyl with the proviso that both R groups cannot be hydrogen; or a pharmaceutically acceptable acid addition salt thereof.

10. A pharmaceutical composition according to claim 9 which further comprises an effective amount of a polyamine oxidase inhibitor as an additional ingredient.

11. A method for the treatment of patients suffering from a neoplastic disease state which comprises administering to said patient a therapeutically effective amount of a compound of the formula:

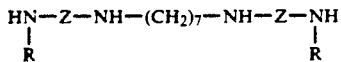

wherein Z is a saturated ($C_2$–$C_6$) alkylene moiety, each R group independently is hydrogen, methyl, ethyl, or n-propyl with the provisos that both R groups cannot be hydrogen and that R is hydrogen or methyl when Z is a branched chain alkylene; or a pharmaceutically acceptable acid addition salt thereof.

12. A method according to claim 11 wherein the neoplastic disease state is a carcinoma comprising carcinoma of the cervix, esophagus, stomach, small intestine, colon, or lungs.

13. A method according to claim 11 wherein the neoplastic disease state is a sarcoma comprising oesteroma, osteosarcoma, lepoma, lyposarcoma, hemangioma, or hemangeosarcoma.

14. A method according to claim 11 wherein the neoplastic disease state is a leukemia comprising lymphoblastic, chronic lymphocytic, acute myoblastic, or chronic mylocytic leukemias.

15. A method according to claim 11 wherein the neoplastic disease state is a melanoma comprising amelanotic or melanotic types.

16. A method according to claim 11 wherein the compound is N,N'-bis[3-(methylamino)butyl]-1,7-diaminoheptane.

17. A method according to claim 11 wherein the compound is N,N'-bis[3-(ethylamino)propyl]-1,7-diaminoheptane.

18. A method according to claim 11 wherein the compound is N,N'-bis[3-(methylamino)propyl]-1,7-diaminoheptane.

19. A method according to claim 11 wherein the compound is N,N'-bis[3-(methylamino)-2-(methyl)-propyl]-1,7-diaminoheptane.

20. A method according to claim 11 which further comprises conjunctive therapy with an effective amount of a polyamine oxidase inhibitor.

21. A method according to claim 20 wherein the polyamine oxidase inhibitor is N,N'-bis(2,3-butanedienyl)-1,4-butanediamine or N-(2,3-butadienyl)-N'-methyl-1,4-butanediamine.

22. A compound of claim 2 wherein the compound is (R,R)-N,N'-bis[3-(methylamino)butyl]-1,7-diaminoheptane.

23. A compound of claim 2 wherein the compound is (S,S)-N,N'-bis[3-(methylamino)butyl]-1,7-diaminoheptane.

24. A compound of claim 2 wherein the compound is (R,S)-N,N'-bis[3-(methylamino)butyl]-1,7-diaminoheptane.

25. A method of inhibiting metastasis in a patient suffering from a malignant tumor which comprises administering to said patient a therapeutically effective amount of a compound of the formula:

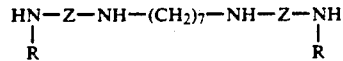

wherein Z is a saturated ($C_2$–$C_6$) alkylene moiety group independently is hydrogen, methyl, ethyl, or n-propyl with the provisos that both R groups cannot be hydrogen and that R is hydrogen or methyl when Z is a branched chain alkylene; or a pharmaceutically acceptable acid addition salt thereof.

26. A method according to claim 25 wherein the compound is N,N'-bis[3-(ethylamino)propyl]-1,7-diaminoheptane.

* * * * *

UNITED STATES PATENT AND TRADEMARK OFFICE
CERTIFICATE OF CORRECTION

PATENT NO. : 5,109,024

DATED : April 28, 1992

INVENTOR(S) : Nellikunja J. Prakash, et al.

Page 1 of 3

It is certified that error appears in the above-identified patent and that said Letters Patent is hereby corrected as shown below:

At Column 1, lines 10 and 15, the patent reads "07/449,559" and should read --07/499,559--.

At Column 2, line 10, the patent reads "when Z ia a branched" and should read --when Z is a branched--.

At Column 2, line 16, the patent reads "formula (Ia) and Ib)" and should read --formula (Ia) and (Ib)--.

At Column 4, line 17, the patent reads "alternatively, compounds of" and should read --Alternatively, compounds of---.

At Column 4, line 19, the patent reads "reductive alkylationusing an" and should read --reductive alkylation using an--.

At Column 4, line 64, the patent reads "a solvent SuCh as DMF," and should read --a solvent such as DMF,--.

At Column 5, line 42, the patent reads "includin but not limited" and should read --including but not limited--.

At Column 5, line 43, the patent reads "cervix, sesophagus" and should read --cervix, esophagus--.

At Column 8, line 39, the patent reads "atoms includin with" and should read --atoms including with--.

At Column 9, line 50, the patent reads "wherein Z1 is an" and should read --wherein $Z_1$ is an--.

At. Column 10, line 54, the patent reads "-CH(C2H5)CH2CH2-" and should read ---$CH(C_2H_5)CH_2CH_2$---.

UNITED STATES PATENT AND TRADEMARK OFFICE
CERTIFICATE OF CORRECTION

PATENT NO. : 5,109,024
DATED : April 28, 1992
INVENTOR(S) : Nellikunja J. Prakash, et al.

It is certified that error appears in the above-identified patent and that said Letters Patent is hereby corrected as shown below:

At Column 11, line 33, the patent reads "until H2 is no longer" and should read --until $H_2$ is no longer--.

At Column 12, line 22, the patent reads "1,18-Bismethyl)-1,5,14,18-" and should read --1,18-Bis(ethyl)-1,5,14,18---.

At Column 12, line 47, the patent reads "of the title 46.09, H-10.10, N-11.95, C1-30.24; Found C-46.23, H-9.94, N-12.11, C1-29.99." and should read --of the title compound, mp >300°C. Elemental analysis: Calculated, C-46.09, H-10.10, N-11.95, C1-30.24; Found C-46.23, H-9.94, N-12.11, C1-29.99.--.

At Column 12, line 60, the patent reads "20% ethyl aCetate/hexane)." and should read --20% ethyl acetate/hexane).---.

At Column 13, line 27, the patent reads "N,N'-bis[(phenYl)" and should read --N,N'-bis[(phenyl)--.

At Column 14, line 14, the patent reads "tetraazaheotadecane" and should read --tetraazaheptadecane--.

UNITED STATES PATENT AND TRADEMARK OFFICE
CERTIFICATE OF CORRECTION

PATENT NO. : 5,109,024

DATED : April 28, 1992

INVENTOR(S) : Nellikunja J. Prakash, et al.

It is certified that error appears in the above-identified patent and that said Letters Patent is hereby corrected as shown below:

At Column 15, line 4, the patent reads "to yield 10 0.90 g of" and should read --to yield 0.90 g of--.

At Column 17, line 34, the patent reads "of Compound in inhibiting" and should read -of Compound 28314 in inhibiting---.

At Column 18, line 19, the patent reads "is hydrogen of methyl" and should read --is hydrogen or methyl--.

At Column 20, line 38, the patent reads "alkylene moiety group" and should read --alkylene moiety, each R group--.

Signed and Sealed this

Sixth Day of September, 1994

BRUCE LEHMAN

*Attest:*

*Attesting Officer*  *Commissioner of Patents and Trademarks*